United States Patent [19]

Rubino et al.

[11] 4,115,553

[45] * Sep. 19, 1978

[54] ANTACID TABLETS

[75] Inventors: Andrew M. Rubino, New Providence; Jack J. Margres, Old Bridge, both of N.J.

[73] Assignee: Armour Pharmaceutical Company, Phoenix, Ariz.

[*] Notice: The portion of the term of this patent subsequent to Sep. 9, 1995, has been disclaimed.

[21] Appl. No.: 482,431

[22] Filed: Jun. 24, 1974

Related U.S. Application Data

[63] Continuation-in-part of Ser. No. 423,226, Dec. 10, 1973.

[51] Int. Cl.² .................... A61K 33/12; A61K 33/10; A61K 33/08
[52] U.S. Cl. .................................. 424/155; 424/156; 424/157; 424/158
[58] Field of Search ................ 424/155, 156, 157, 158

[56] References Cited

U.S. PATENT DOCUMENTS

| | | | |
|---|---|---|---|
| 3,272,704 | 9/1966 | Beekman | 424/158 |
| 3,579,634 | 5/1971 | Brown | 424/156 |
| 3,599,150 | 8/1971 | Feinberg et al. | 424/158 |
| 3,639,168 | 2/1972 | Monti et al. | 424/156 |
| 3,639,169 | 2/1972 | Broeg et al. | 424/156 |

FOREIGN PATENT DOCUMENTS 45-26,518  1/1970  Japan ..................................... 424/158

*Primary Examiner*—Frederick E. Waddell
*Attorney, Agent, or Firm*—Richard R. Mybeck; C. C. Batz

[57] ABSTRACT

Antacid tablets prepared by codrying certain basic aluminum bicarbonate-carbonate compositions with di- or trihydroxy alcohols suitable for oral ingestion, to obtain a powder material, and forming such a material suitably along with tablet forming ingredients into tablets which have superior mouth feel and which yield faster reaction velocities than prior antacid tablets.

11 Claims, No Drawings

ANTACID TABLETS

RELATED APPLICATIONS

This application is a continuation-in-part of our application Ser. No. 423,226 filed Dec. 10, 1973.

This invention relates to antacid tablets and more particularly to tablets which contain compositions formed by codrying certain basic aluminum bicarbonate-carbonate compositions with certain di- or trihydroxy alcohols, and to processes for the preparation of such tablets.

BACKGROUND

Aluminum hydroxide gel is a standard therapeutic for the treatment of peptic ulcer and other symptoms of gastro hyperacidity. Liquid aluminum hydroxide gel closely approaches the ideal for an antacid. However, its liquid form makes it inconvenient to use, especially in the case of ambulatory patients. It would be very desirable to have the advantages of such a gel in dried form, but unfortunately aluminum hydroxide gel undergoes undesirable change on drying during its manufacture and further changes upon aging of the dried material. In the dry solid form it exhibits a lag in its rate of reaction with stomach acid and does not give a prolonged acid effect in the optimum pH range. In addition, its antacid properties are severely affected by pepsin and its activity is less than that of the liquid gel.

In our copending patent application Ser. No. 423,226 filed Dec. 10, 1973 we disclose antacid compositions prepared by codrying basic aluminum bicarbonate-carbonates with certain di- or trihydroxy alcohols to form dried gel compositions which are readily resuspendable to yield the same characteristics as the original liquid gels.

SUMMARY OF THE INVENTION

We have now discovered that the compositions above referred to prepared by codrying basic aluminum bicarbonate-carbonate and a water soluble foodgrade di- or trihydroxy alcohol suitable for oral ingestion may be formed into chewable tablets which yield faster reaction velocities, more rapid disintegration rates and improved reactivity over previously available antacid tablets. Further, the improved tablets have a superior mouth feel, are gritfree, melt readily in the mouth and do not have the chalkiness associated with the well-known $Al(OH)_3$ antacid tablets. In addition the improved tablets require less water in wet granulation resulting in a shorter drying cycle in the preparation of the tablets.

DETAILED DESCRIPTION

The preparation of our improved antacid tablets involves first the preparation of the powdered material by codrying the essential ingredients and then formulating and compressing this material into tablets.

Preparation of Antacid Powder

We start with any available aluminum hydroxide gel provided the gel is a wet gel which has not been predried and which is highly reactive, freshly precipitated aluminum hydroxide containing carbonate. Such aluminum hydroxide gel compounds are distinguished from the inert grade of aluminum hydroxide in which only aluminum and hydroxy and/or oxy entities are present by the fact that they are oxy- hydroxy bicarbonate-carbonate type of aluminum compounds. Each such compound is prepared by an alkaline precipitating reagent which contains either bicarbonate or carbonate as its anion. Each of the typical "reactive-grade aluminum hydroxide" compressed gels employed in the improved antacid materials either alone or in combination with other buffering entities, such as, for example, magnesium and/or calcium hydroxides, carbonates, silicates, and in some instances sodium and other compounds, are in reality, mixed, complex, amorphous and highly hydrated systems of aluminum hydroxy carbonates and bicarbonates. Such compounds are distinguished from inert aluminum hydroxide by simple carbon dioxide evolution analysis. These compounds have at least 0.2 and preferably 0.5 mole of carbonate calculated as $CO_2$ for each mole of aluminum oxide. The analysis of the dried product yields a figure in the range from 30 to 60% by weight for the sum of aluminum hydroxide and magnesium hydroxide calculated as $Al_2O_3$ and $MgO$. A preferred magnesium hydroxide gel is a 30% magnesium hydroxide paste obtained by controlled precipitation from pure aqueous solutions of magnesium sulfate and sodium hydroxide followed by filtration, washing and mixing the washed hydrogel. Other forms of $Mg(OH)_2$ may be used, such as the dolomitic lime (CaO-MgO) precipitate of $MgCl_2$.

In carrying out the procedure for the preparation of the antacid powder, the aluminum hydrate gel as above described may be mixed with the alcohol and stirred for an hour or more and the suspension then dried, preferably by spray drying, but drum, or other drying methods may be used. The product is a soft, finely divided, white powder.

Preparation of Tablets

The powder prepared as above described may be formed into tablets along with other ingredients and preferably is contained in the tablet formulation to the extent of 10 to 90% by weight of the tablet. Other ingredients which may be included are: Mannitol which may be used to enhance the compressibility of the tablet. Mannitol is preferred because of its negative heat of solution, which yields a cooling effect in the mouth. The mannitol may simply be included in the amount of from 4 to 89% based on weight. Sucrose, lactose or sorbitol are examples of many other excipients that may be used instead of or along with mannitol.

Glycine which may be used as a flavor modifier and possible contributor to antacid properties; a crystalline cellulose, such as Avicel PH101, may be used as a disintegrant to assist in getting the tablet to break apart in an aqueous environment; sodium saccharin may be added as a sweetener; and magnesium stearate may be added as a lubricant to keep the tablet from sticking to the die wall. Other antacids may be added such as $Mg(OH)_2$, $CaCO_3$, and dihydroxy aluminum sodium carbonate (DASC). We prefer that manitol be combined with the codried powder in the formulation of our tablet.

To form the tablets the special aluminum hydrate gel powder above described may be placed in a blender such as a twin shell blender along with other powder ingredients, and the mixture blended for a few minutes. Then water or a water solution containing a bonding agent is added to the granulation and the blending continued to obtain proper wetness according to the knowledge of this art. If saccharin is contained in the formula this may first be added to the water. The blend is dried to remove added water and then passed through a screen. To the screened powder may be added items such as Mg stearate and flavoring agents. The blend may then be compressed into tablets according to the usual practice. Following are specific examples demonstrating preferred formulation of the tablets and the characteristics of our improved antacid tablets.

EXAMPLE 1

Preparation of Antacid Powder 3000 grams of aluminum hydroxide compressed gel (10% $Al_2O_3$) which is the commercial gel designated F-1000 by the Reheis Chemical Company, and 3000 grams of glycerin were placed into a ten liter battery jar and put into suspension using a Lightnin' Overhead Stirrer employing a 4-inch, 6-blade, turbine-agitator, set at medium speed. Upon attainment of a homogeneous suspension (approximately 5 minutes), the agitator speed was set at high speed and the suspension stirred rapidly at ambient temperatures for two hours. The batch was then spray dried in a Bowen three foot, flat bottom laboratory spray dryer employing an outlet temperature of 270° F. and a feed rate of 100 ml per minute. About one pound of a soft, finely divided, white powder was obtained which analyzed as follows:

| | |
|---|---|
| $Al_2O_3$ | 25.7% |
| Glycerin | 59.3% |
| Apparent density | 0.36 g/cc |

EXAMPLE 2

Preparation of Antacid Powder 4 part Reheis F-1000 compressed gel USP (10% $Al_2O_3$), 1 part 1:3 butylene glycol, foodgrade, and three parts of deionized water were placed into suspension form and stirred rapidly at ambient temperatures for two hours. The suspension was then spray dried at 200 ml per minute employing an outlet temperature of 270° F. A finely divided white powder was obtained analyzing as follows:

| | |
|---|---|
| $Al_2O_3$ | 44.3% |
| 1:3 Butylene Glycol | 22.9% |
| Apparent density grams per ml | 0.18 |

EXAMPLE 3

Preparation of Antacid Powder

The procedure of Example 2 was duplicated except that Reheis F-500 compressed gel USP was used in lieu of the F-1000 gel, and propylene glycol USP was used in lieu of 1:3 butylene glycol. The F-500 compressed gel refers to a specific basic aluminum bicarbonate-carbonate gel marketed by Reheis Chemical Company.

An approximately ¾ pound yield of a soft, finely divided, white powder was obtained with the following assay:

| | |
|---|---|
| $Al_2O_3$ | 43.5% |
| Propylene Glycol | 26.0% |
| Apparent Density in grams per cc | 0.3% |

EXAMPLE 4

Preparation of Antacid Powder

We may repeat the procedure of Example 2, using, instead of 1:3 butylene glycol, a polyethylene glycol having a molecular weight in the range of about 200–700, and obtain a soft, finely divided, white powder which is satisfactory for use in the practice of our invention.

EXAMPLE 5

Preparation of Antacid Powder

We may repeat the procedure of Example 1, using, instead of F-1000 a wet compressed gel marketed by Reheis Chemical Company under the designation F-2000 or F-X gel. The F-2000 is a U.S.P. grade aluminum hydroxide compressed gel containing approximately 13.0% $Al_2O_3$ and similar in chemical structure to Reheis F-1000 Compressed Gel U.S.P. The F-X gel is obtained essentially by reversing the order of addition used in the preparation of the F-1000 gel. In the production of F-1000 gel $AlCl_3$ is added to soda ash (acid to base) while F-X gel requires the addition of soda ash to $AlCl_3$ (base to acid).

EXAMPLE 6

Preparation of Antacid Gel

The procedure of Example 1 may be repeated using instead of the F-1000 gel a gel being marketed by Reheis Chemical Company under the designation of F-MA11. This gel is a combined gel of basic aluminum bicarbonate-carbonate and magnesium basic carbonate (U.S. Pat. No. 2,797,978) or we may use a combination of F-1000 and magnesium hydroxide ($Mg(OH)_2$), and in each case we obtain a soft, finely divided, white powder which is satisfactory for use in the practice of our invention.

EXAMPLE 7

Preparation of Antacid Tablet

Tablets were made using the following ingredients in the proportion stated:

| | | Parts/wt. |
|---|---|---|
| 1. | F-1000-Glycerin (the powder obtained by Example 1) | 50.0 |
| 2. | Mannitol USP | 29.0 |
| 3. | Sorbitol USP | 7.72 |
| 4. | Avicel PH101 (a microcrystalline cellulose) | 11.7 |
| 5. | Sodium Saccharin | 0.08 |
| 6. | Magnesium Stearate | 1.5 |
| 7. | Flavoring Agent | q.s. |

The F-1000-Glycerin powder, mannitol, sorbitol and Avicel were blended in a twin shell blender for 15 minutes. The saccharin was dissolved in water and the water used as a wetting agent for this granulation. The water was added to the blend until proper wetness was obtained using a Hobart mixer as a blender.

The blend was dried for 16 hours at 50° F. and passed through a #12 screen. The magnesium stearate and flavoring agent were then added and the mix compressed into tablets.

EXAMPLE 8

Preparation of Antacid Tablet

Tablets were made using the following ingredients.

|    |                | parts/wt. |
|----|----------------|-----------|
| 1. | F-1000-Glycerin | 21.4     |
| 2. | Mg(OH)$_2$ pdr. | 19.4     |
| 3. | Mannitol        | 32.8     |
| 4. | Sorbitol        | 8.3      |
| 5. | Avicel PH101    | 15.6     |
| 6. | Na Saccharin    | 0.1      |
| 7. | Mg Stearate     | 2.0      |
| 8. | Flavoring agent | 0.4      |

Ingredients Nos. 1–5 above, were blended in a twin shell blender for 15 minutes, # 6 dissolved in water and the water added to the blend using a Hobart mixer, followed by drying for 16 hours at 50° F. The blend was then passed through a #12 screen, the items Nos. 7 and 8 then added, and the blend compressed into tablets.

EXAMPLE 9

Preparation of Antacid Tablets

|    |                 | parts/wt. |
|----|-----------------|-----------|
| 1. | F-1000-Glycerin | 25.7      |
| 2. | Mg(OH)$_2$ pdr. | 14.8      |
| 3. | CaCO$_3$ pdr.   | 9.5       |
| 4. | Mannitol        | 29.0      |
| 5. | Sorbitol        | 8.5       |
| 6. | Avicel PH101    | 11.6      |
| 7. | Na Saccharin    | 0.1       |
| 8. | Mg Stearate     | 0.5       |
| 9. | Flavoring agent | 0.3       |

Items 1–6 were blended, item 7 dissolved in water and the resultant solution added to the blend followed by drying, screening, addition of items 8 and 9 and compressing.

EXAMPLE 10

Preparation of Antacid Tablets

|    |                                 | parts/wt. |
|----|---------------------------------|-----------|
| 1. | F-1000-Glycerin                 | 10.0      |
| 2. | Dihydroxyaluminum Sodium Carbonate | 29.9   |
| 3. | Mannitol                        | 29.0      |
| 4. | Sorbitol                        | 17.5      |
| 5. | Avicel PH101                    | 11.7      |
| 6. | Na Saccharin                    | 0.1       |
| 7. | Mg Stearate                     | 1.5       |
| 8. | Flavoring Agent                 | 0.3       |

Items 1–5 were blended, item 6 dissolved in water and the resultant solution added to the blend as outlined in Example 8 to form the completed tablet.

EXAMPLE 11

Preparation of Antacid Tablets

Tablets were made using the following ingredients:

|    |                 | parts/wt. |
|----|-----------------|-----------|
| 1. | F-1000-Glycerin | 14.1      |
| 2. | Mg Trisilicate  | 19.3      |
| 3. | Mannitol        | 38.6      |
| 4. | Sorbitol        | 10.0      |
| 5. | Avicel PH101    | 15.6      |
| 6. | Na Saccharin    | 0.1       |
| 7. | Mg Stearate     | 2.0       |

-continued

|    |                 | parts/wt. |
|----|-----------------|-----------|
| 8. | Flavoring Agent | 0.3       |

Items 1–5 were blended, the saccharin dissolved in water, the resultant solution, etc. as in Example 8.

EXAMPLE 12

Preparation of Antacid Tablets

Tablets were made using the following ingredients:

|    |                 | parts/wt. |
|----|-----------------|-----------|
| 1. | F-1000-Glycerin | 21.0      |
| 2. | Mg Glycinate    | 29.0      |
| 3. | Mannitol        | 29.0      |
| 4. | Sorbitol        | 8.6       |
| 5. | Avicel PH101    | 11.5      |
| 6. | Na Saccharin    | 0.1       |
| 7. | Mg Stearate     | 0.5       |
| 8. | Flavoring Agent | 0.3       |

Items 1, 2, 3 and 5 were blended, items 4 and 6 dissolved in water, and the resultant solution added and the procedure carried through as in Example 8 to obtain a finished tablet.

EXAMPLE 13

Preparation of Antacid Tablets

Although Example 6 to 12 utilized the codried material of Example 1, the codried powder of any of Examples 1 to 5 may be utilized in the same way to obtain an improved antacid tablet.

EXAMPLE 14

Preparation of Antacid Tablets

Tablets were made using the following ingredients:

|    |                 | parts/wt. |
|----|-----------------|-----------|
| 1. | F-MA11-Glycerin | 33.3      |
| 2. | Mannitol USP    | 38.6      |
| 3. | Sorbitol        | 10.0      |
| 4. | Avicel PH101    | 15.6      |
| 5. | Na Saccharin    | 0.1       |
| 6. | Mg Stearate     | 2.0       |
| 7. | Flavoring Agent | 0.4       |

Items 1, 2, 3 and 4 were blended, item 5 dissolved in water and the resultant solution added and the process carried through as in Example 8 to form a finished tablet.

EXAMPLE 15

Preparation of Antacid Tablets

Tablets were made using the following ingredients:

|    |                 | parts/wt. |
|----|-----------------|-----------|
| 1. | F-MA11-Glycerin | 33.3      |
| 2. | Sucrose         | 48.6      |
| 3. | Avicel PH101    | 15.6      |
| 4. | Na Saccharin    | 0.1       |
| 5. | Mg Stearate     | 2.0       |
| 6. | Flavoring Agent | 0.4       |

Items 1, 2 and 3 were blended, item 4 dissolved in water and the resultant solution added and the process carried through as in Example 8 to form a finished tablet.

EXAMPLE 16

Preparation of Antacid Tablets

Tablets were made using the following ingredients:

| | | parts/wt. |
|---|---|---|
| 1. | F-MA11-Glycerin | 33.5 |
| 2. | Mannitol | 20.0 |
| 3. | Sorbitol | 10.4 |
| 4. | Avicel PH101 | 18.0 |
| 5. | Glycine | 16.0 |
| 6. | Na Saccharin | 0.1 |
| 7. | Mg Stearate | 1.5 |
| 8. | Flavoring Agent | 0.5 |

Items 1, 2, 3 and 4 were blended, items 5 and 6 dissolved in water and the resultant solution added, etc., the process being continued as in Example 8 to form a finished tablet.

EXAMPLE 17

Preparation of Antacid Tablets

Tablets were made using the following ingredients:

| | | parts/wt. |
|---|---|---|
| 1. | F-MA11-Glycerin | 28.3 |
| 2. | Mg(OH)$_2$ pdr. | 21.6 |
| 3. | Mannitol | 29.0 |
| 4. | Sorbitol | 7.0 |
| 5. | Avicel PH101 | 11.5 |
| 6. | Na Saccharin | 0.8 |
| 7. | Mg Stearate | 1.5 |
| 8. | Flavoring Agent | 0.3 |

Items 1 to 5 were blended, item 6 dissolved in water and the process continued as in Example 8 to form a finished tablet.

EXAMPLE 18

Preparation of Antacid Tablets

Tablets were made using the following ingredients:

| | | parts/wt. |
|---|---|---|
| 1. | F-MA11-Glycerin | 27.0 |
| 2. | Mg Trisilicate | 23.0 |
| 3. | Mannitol | 29.0 |
| 4. | Sorbitol | 7.5 |
| 5. | Avicel PH101 | 11.7 |
| 6. | Na Saccharin | 0.8 |
| 7. | Mg Stearate | 1.5 |
| 8. | Flavoring Agent | 0.3 |

Items 1, 2, 3 and 5 were blended, items 4 and 6 dissolved in water and the resultant solution added, etc., the process being continued as in Example 8 to form a finished tablet.

EXAMPLE 19

Preparation of Antacid Tablets

Tablets were made using the following ingredients:

| | | parts/wt. |
|---|---|---|
| 1. | F-1000 Mg(OH)$_2$ Glycerin | 50.0 |
| 2. | Mannitol | 29.0 |
| 3. | Sorbitol | 7.5 |
| 4. | Avicel PH101 | 11.6 |
| 5. | Na Saccharin | 0.1 |
| 6. | Mg Stearate | 1.5 |
| 7. | Flavoring Agent | 0.3 |

Items 1, 2, 3 and 4 were blended, item 6 dissolved in water, the resultant solution added to the blend, etc., the process being continued as in Example 8 to form a finished tablet.

EXAMPLE 20

Preparation of Antacid Tablet

Tablets were made using the following ingredients:

| | | parts/wt. |
|---|---|---|
| 1. | F-MA11 Glycerin -glycine (Al$_2$O$_3$: Glycerin : glycine:: 3:1:1) | 33.6 |
| 2. | Mannitol USP | 39.0 |
| 3. | Avicel PH101 | 15.8 |
| 4. | Glycine | 10.1 |
| 5. | Na Saccharin | 0.1 |
| 6. | Mg Stearate | 1.0 |
| 7. | Flavoring Agent | 0.4 |

Items 1, 2 and 3 were blended, items 4 and 5 dissolved in water, the resultant solution added to the blend, etc., the process being continued as in Example 8 to form a finished tablet.

EXAMPLE 21

Preparation of Antacid Tablets

Tablets were made using the following ingredients:

| | | parts/wt. |
|---|---|---|
| 1. | F-MA11 Propylene glycol | 33.6 |
| 2. | Mannitol USP | 39.0 |
| 3. | Avicel PH101 | 15.8 |
| 4. | Glycine | 10.1 |
| 5. | Na Saccharin | 0.1 |
| 6. | Mg Stearate | 1.0 |
| 7. | Flavoring Agent | 0.4 |

These ingredients were combined and the procedure carried out as in Example 20, above.

EXAMPLE 22

Preparation of Antacid Tablets

Tablets were made using the following ingredients:

| | | parts/wt. |
|---|---|---|
| 1. | F-MA11-1,3-butylene glycol | 33.6 |
| 2. | Mannitol USP | 39.0 |
| 3. | Avicel PH101 | 15.8 |
| 4. | Glycine | 10.1 |
| 5. | Na Saccharin | 0.1 |
| 6. | Mg Stearate | 1.0 |
| 7. | Flavoring Agent | 0.4 |

These ingredients were combined and the procedure carried out as in Example 20, above.

EXAMPLE 23

Preparation of Antacid Tablets

| | | parts/wt. |
|---|---|---|
| 1. | F-MA11-polyethylene glycol | 33.6 |
| 2. | Mannitol USP | 39.0 |
| 3. | Avicel PH101 | 15.8 |
| 4. | Glycine | 10.1 |
| 5. | Na Saccharin | 0.1 |
| 6. | Mg Stearate | 1.0 |
| 7. | Flavoring Agent | 0.4 |

These ingredients were combined and the procedure carried out as in Example 20, above.

EXAMPLE 24

Comparison with Prior Tablets

To compare tablets made using the special codried aluminum hydroxide material with tablets made using regular aluminum hydroxide we made two formulations just alike, except that in the formulation A we used the special codried powder, and in formulation B were used the same powder, but not codried with a di- or trihydroxide alcohol. The formulations were as follows:

| Formulation A | | Formulation B | |
|---|---|---|---|
| Ingredients | Parts/wt. | Ingredients | Parts/wt. |
| F-MA11-Glycerin | 50.0 | F-MA11 Powder | 50.0 |
| Lactose | 47.6 | Lactose | 47.6 |
| Mg Stearate | 2.0 | Mg Stearate | 2.0 |
| Flavoring Agent | 0.4 | Flavoring Agent | 0.4 |

In each case the active ingredient and 80% of the lactose employed were dry blended. The remaining lactose was dissolved in water and the resultant solution was added to each individual blend until proper wetness was obtained, the process then being continued as in Example 8 to form a finished tablet.

In the forming procedure it took about 25% less water to produce proper wetness in the case of Formulation A. Formulation B yielded tablets which were so gritty that they would be considered borderline so far as palatability is concerned. Tablets of Formulation A were smooth, not gritty, and had a much superior mouth feel, dissolving faster in the mouth.

EXAMPLE 25

Comparison with Prior Tablets

Example 24 was duplicated with the exception that F-1000 Glycerin was used in lieu of F-MA11-Glycerin in Formulation A and F-1000 Powder was employed in place of F-MA11 Powder in Formulation B.

As in Example 24 approximately 25% less water was needed to yield a proper wetness in Formulation A, and tablets prepared with Formulation A were smoother, less gritty, and dissolved faster and had a superior mouth feel to companion tablets prepared with Formulation B.

While the foregoing description and examples exemplify specific ways in which our invention may be carried out, it is understood that these are illustrative only and that the practice of the invention may take many and varied forms all within the spirit and scope of the invention and the appended claims.

We claim:

1. An antacid tablet comprising the codried combination of a hydrous gelatinous aluminum hydroxide material with an alcohol, and an excipient therefor, said material being selected from the group consisting of:
   (1) basic aluminum bicarbonate-carbonate and
   (2) basic aluminum bicarbonate-carbonate in combination with magnesium basic carbonate, magnesium hydroxide, or magnesium trisilioate, or mixtures thereof, said alcohol being a foodgrade di- or trihydroxy alcohol suitable for oral ingestion, wherein analysis of the codried combination yields a figure of from 30 to 60 weight percent for the sum of the aluminum hydroxide and magnesium hydroxide calculated as $Al_2O_3$ and MgO and shows that there is present at least 0.3 mole of carbonate calculated as $CO_2$ for each mole of $Al_2O_3$, said codried combination being contained in the tablet in an amount of from 10 to 90 weight percent of the tablet.

2. The tablet of claim 1 which contains mannitol in addition to said codried combination.

3. The tablet of claim 1 which contains as a bulking agent and disintegrant a crystalline cellulose.

4. The tablet of claim 1 wherein said alcohol is glycerin.

5. The tablet of claim 1 wherein said alcohol is 1:2 propylene glycol.

6. The tablet of claim 1 wherein said alcohol is 1:3 butylene glycol.

7. A process for the preparation of antacid tablets comprising codrying a hydrous gelatinous aluminum hydroxide material selected from the group consisting of:
   (1) basic aluminum bicarbonate-carbonate, and
   (2) basic aluminum bicarbonate-carbonate in combination with magnesium basic carbonate, magnesium hydroxide, or magnesium trisilicate, or mixtures thereof, and a foodgrade di- or trihydroxy alcohol suitable for oral ingestion, to obtain a codried combination which yields a figure of from 30 to 60 weight percent for the sum of aluminum hydroxide and magnesium hydroxide calculated as $Al_2O_3$ and MgO and shows that there is present at least 0.3 mole of carbonate calculated as $CO_2$ for each mole of $Al_2O_3$, and compressing said codried combination into tablets.

8. In a process for the preparation of antacid tablets, the improvement which comprises the step of compressing a powder which is a codried composition of wet aluminum hydroxide gel and a foodgrade di- or trihydroxy alcohol suitable for oral ingestion and which contains from 30 to 60 percent $Al_2O_3$ and at least 0.3 mole of carbonate calculated as $CO_2$ for each mole of $Al_2O_3$, to form a tablet.

9. The process of claim 7 in which said codried composition contains from 5 to 50 percent foodgrade alcohol.

10. The process of claim 7 in which said alcohol is glycerin.

11. An antacid tablet comprising the codried combination of a hydrous gelatinous aluminum hydroxide material with an alcohol, and an excipient therefor, said material being selected from the group consisting of:
    (1) basic aluminum bicarbonate-carbonate and
    (2) basic aluminum bicarbonate-carbonate in combination with magnesium basic carbonate, magnesium hydroxide, or magnesium trisilicate, or mixtures thereof, said alcohol being polyethylene glycol having a molecular weight of about 200 to 700, wherein analysis of the codried combination yields a figure of from 30 to 60 weight percent for the sum of the aluminum hydroxide and magnesium hydroxide calculated as $Al_2O_3$ and MgO and shows that there is present at least 0.3 mole of carbonate calculated as $CO_2$ for each mole of $Al_2O_3$, said codried combination being contained in the tablet in an amount of from 10 to 90 weight percent of the tablet.

* * * * *